United States Patent [19]
Yamamoto et al.

[11] Patent Number: 4,742,177
[45] Date of Patent: May 3, 1988

[54] METHACRYLIC ACID ESTER

[75] Inventors: Yasushi Yamamoto; Hironao Fujiki; Hideto Kato, all of Takasaki; Akira Yoshida, Annaka, all of Japan

[73] Assignee: Shin-Etsu Chemical Co., Ltd., Tokyo, Japan

[21] Appl. No.: 8,538

[22] Filed: Jan. 29, 1987

[30] Foreign Application Priority Data

Jan. 31, 1986 [JP] Japan .................................. 61-19399

[51] Int. Cl.$^4$ .............................................. C07F 7/10
[52] U.S. Cl. ................................................... 556/419
[58] Field of Search ......................................... 556/419

[56] References Cited

U.S. PATENT DOCUMENTS

| 3,646,085 | 2/1972 | Bartlett | 556/419 |
| 3,950,588 | 4/1976 | McDougal | 556/419 X |
| 4,094,911 | 6/1978 | Mitsch et al. | 556/419 X |
| 4,647,413 | 3/1987 | Savu | 556/419 X |

FOREIGN PATENT DOCUMENTS

| 58-127914 | 7/1983 | Japan | 556/419 |
| 58-164672 | 9/1983 | Japan | 556/419 |
| 58-167597 | 10/1983 | Japan | 556/419 |

*Primary Examiner*—Paul F. Shaver
*Attorney, Agent, or Firm*—Schwartz, Jeffery, Schwaab, Mack, Blumenthal & Evans

[57] ABSTRACT

A novel methacrylic acid ester represented by General Formula (I):

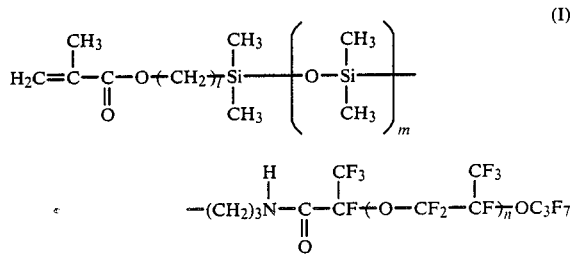

wherein l is an integer of 1 to 3; m is an integer of 1 to 10; and n is an integer of 1 to 3, and a process for producing the same. This novel methacrylic acid ester is useful for the synthesis of polymers having useful functions such as an oxygen enrichment performance.

3 Claims, No Drawings

METHACRYLIC ACID ESTER

BACKGROUND OF THE INVENTION

1. Field of the Invention

This invention relates to a novel methacrylic acid ester, and, particularly, to a novel methacrylic acid ester useful for the synthesis of a polymer having useful functions such as an oxygen enrichment performance.

2. Description of the Prior Art

Heretofore, there are known methacrylic acid esters having a poly(perfluoroalkylene glycol) group in its alcohol residual group (see Japanese Laid-open Patent Publications No. 127914/1983 and No. 164672/1983), but there is unknown a methacrylic acid ester having both a siloxy group and a poly(perfluoroalkylene glycol) group in its alcohol residual group.

SUMMARY OF THE INVENTION

An object of this invention is to provide a methacrylic acid ester having both a siloxy group and a poly(perfluoroalkylene glycol) group in its alcohol residual group.

This invention provides a methacrylic acid ester represented by General Formula (I):

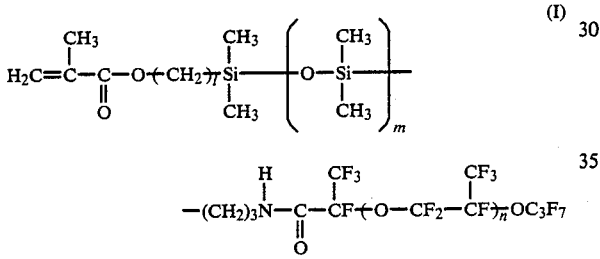

wherein $l$ is an integer of 1 to 3; $m$ is an integer of 1 to 10; and $n$ is an integer of 1 to 3.

The methacrylic acid ester of this invention contains a vinyl group, and is capable of being homopolymerized or capable of being copolymerized with other copolymerizable monomers. A resulting polymer has a siloxy group and a poly(perfluoroalkylene glycol) group, among which the siloxy group has an action to enhance the flexibility and oxygen permeability of the polymer and the poly(perfluoroalkylene glycol) group has an action to enhance the toughness and oxygen permeability of the polymer. Accordingly, the methacrylic acid ester of this invention is very useful for the production of polymer materials which is flexible and tough and has useful functions such as an oxygen enrichment performance.

DETAILED DESCRIPTION OF THE INVENTION

Synthesis of this methacrylic acid ester can be carried out, as shown, for example, in the reaction scheme shown below, by reacting an acid fluoride of poly(hexafluoropropylene glycol) represented by Formula (II) with allylamine to produce an N-allyl acid amide represented by Formula (III), followed by reacting the N-allyl acid amide with a methacrylic acid ester having a silicon-bonded hydrogen atom

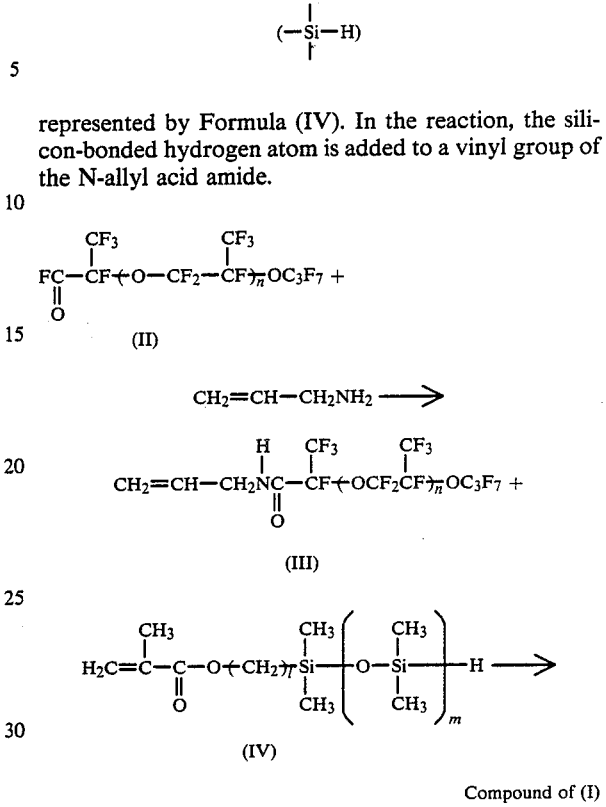

Compound of (I)

Here, $l$, $m$ and $n$ are as defined above.

Synthesis of the acid fluoride of poly(hexafluoropropylene glycol) represented by Formula (II) and synthesis of the N-allyl acid amide represented by Formula (III) obtained by the reaction of said acid fluoride with allylamine can be carried out according to a conventional method.

Namely, the acid fluoride of Formula (II) can be obtained by polymerizing hexafluoropropylene oxide according to the method disclosed in Japanese Patent Publication No. 11061/1965, followed by fractionating, by distillation, a polymer having a desired polymerization degree.

The N-allyl acid amide of Formula (III) can be obtained by, for example, dropwise adding at room temperature the acid fluoride of Formula (II) to a reactor charged with allylamine and triethylamine.

Also, the reaction of the N-allyl acid amide of Formula (III) with the methacrylic acid ester having a silicon-bonded hydrogen atom of Formula (IV) is an application of known addition reactions utilizing a platinum catalyst such as chloroplatinic acid, and can be carried out at 80° to 110° C. in a suitable solvent such as toluene, xylene, benzene or the like, or without a solvent.

EXAMPLES

This invention will be described below in more detail with reference to Examples, but by no means limited to these.

EXAMPLE 1

Into a reactor, 19 g (0.33 mol) of allylamine and 33 g (0.33 mol) of triethylamine were charged, and then 150 g (0.30 mol) of an acid fluoride represented by Formula:

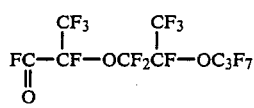

(II, n = 1)

obtained by polymerization of hexafluoropropylene oxide was dropwise added thereto at room temperature. The mixture was then stirred at 40° to 50° C. for 2 hours, and thereafter the reaction mixture was washed with water, and dried, followed by distillation to obtain 124 g of N-allyl acid amide (III, n=1) having a boiling point of 69° to 70° C./3 mmHg.

To 124 g (0.23 mol) of the resulting N-allyl acid amide, 0.1 g of dibutylhydroxytoluene (BHT) and 1 ml of a toluene solution containing 1% of chloroplatinic acid were added, and the mixture was heated to 90° C. and 56 g (0.22 mol) of a methacrylic acid ester represented by Formula:

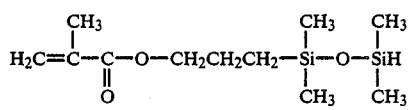

(IV; l = 3, m = 1)

was dropwise added thereto. After the addition, the mixture was stirred for further 1 hour, and thereafter cooled, followed by distillation of the reaction mixture to obtain 101 g of a fraction having a boiling point of 140° to 141° C./$2 \times 10^{-5}$ mmHg (yield: 58%).

On this fraction, measurements of an infrared absorption spectrum and NMR spectrum and elementary analysis were carried out to obtain the results shown below. From the results, this fraction was identified to be a compound represented by the following formula:

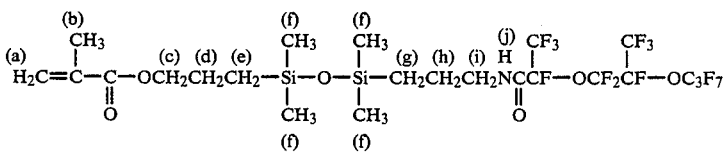

where (a) to (j) indicate the respective protons (indicating the same hereinafter in this example).

Infrared absorption spectrum: cm$^{-1}$: 3350 (acid amide >NH), 1720 (ester >C=O), 1710 (acid amide >C=O), 1640 (vinyl >C=CH$_2$).

NMR spectrum: ppm δ (in CHCl$_3$; CHCl$_3$ internal standard; the same conditions were used hereinafter): 7.57 (broad s, 1H, (j)), 5.97 (s, 1H, (a)), 5.40 (s, 1H, (a)), 4.10-3.85 (t, 2H, (c)), 3.43-3.02 (m, 2H, (i)), 1.80 (s, 3H, (b)), 1.70-1.20 (m, 4H, (d), (h)), 0.73-0.10 (m, 4H, (e), (g)), −0.03 (s, 12H, (f)).

| Elementary analysis: % | | | | |
|---|---|---|---|---|
| | C | H | Si | F |
| Calculated: | 34.72 | 3.80 | 7.06 | 40.59 |
| Found: | 34.44 | 3.74 | 7.14 | 40.47 |

EXAMPLE 2

The procedure of Example 1 was repeated except that 200 g (0.30 mol) of an acid fluoride represented by Formula:

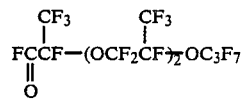

(II, n = 2)

was used in place of the acid fluoride used in Example 1, to obtain 122 g of N-allyl acid amide (III, n=2).

To 108 g (0.15 mol) of the resulting N-allyl acid amide, 0.1 g of BHT and 1 ml of a toluene solution containing 1% of chloroplatinic acid were added, and the mixture was heated to 90° C. and 46 g (0.17 mol) of the methacrylic acid ester having a silicon-bonded hydrogen atom used in Example 1, was dropwise added thereto. After the addition, the mixture was stirred for further 1 hour, and thereafter cooled, followed by distillation of the reaction mixture to obtain 100 g of a fraction having a boiling point of 145° to 146° C./$2 \times 10^{-5}$ mmHg (yield: 68%).

On this fraction, measurements of an infrared absorption spectrum and NMR spectrum and elementary analysis were carried out to obtain the results shown below. From the results, this fraction was identified to be a compound represented by the following formula:

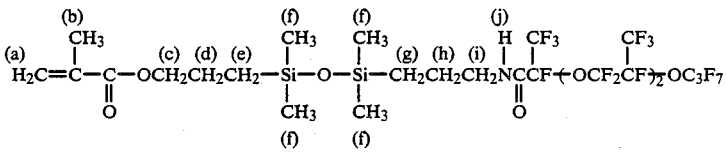

where (a) to (j) indicate the respective protons (indicating the same hereinafter in this example).

Infrared absorption spectrum: cm$^{-1}$: 3350 (acid amide >NH), 1720 (ester >C=O), 1710 (acid amide >C=O), 1640 (vinyl >C=CH$_2$).

NMR spectrum: ppm (δ): 7.66 (broad s, 1H, (j)), 5.90 (s, 1H, (a)), 5.30 (s, 1H, (a)), 4.03-3.80 (t, 2H, (c)), 3.40-2.94 (m, 2H, (i)), 1.73 (s, 3H, (b)), 1.65-1.16 (m, 4H, (d), (h)), 0.63-0.03 (m, 4H, (e), (g)), −0.1 (s, 12H, (f)).

| Elementary analysis: % | | | | |
|---|---|---|---|---|
| | C | H | Si | F |
| Calculated: | 32.47 | 3.14 | 5.84 | 45.44 |

-continued

| | Elementary analysis: % | | | |
|---|---|---|---|---|
| | C | H | Si | F |
| Found: | 32.40 | 3.03 | 5.72 | 45.54 |

EXAMPLE 3

The procedure of Example 1 was repeated except that the amount of allylamine used was changed to 16 g (0.28 mol) and 200 g (0.24 mol) of an acid fluoride represented by Formula:

$$\underset{O}{\underset{\|}{FCCF}}(OCF_2CF)_{\overline{3}}OC_3F_7$$
$$\overset{|}{CF_3} \quad \overset{|}{CF_3}$$

(II, n = 3)

was used in place of the acid fluoride used in Example 1, to obtain 104.4 g of N-allyl acid amide (III, n=3).

To 95 g (0.11 mol) of the resulting N-allyl acid amide, 0.1 g of BHT and 1 ml of a toluene solution containing 1% of chloroplatinic acid were added, and the mixture was heated to 90° C. and 30 g (0.12 mol) of the same methacrylic acid ester having a silicon-bonded hydrogen atom as used in Example 1 was dropwise added thereto. After the addition, the mixture was stirred for further 1 hour, and thereafter cooled, followed by distillation of the reaction mixture to obtain 77 g of a fraction having a boiling point of 163° to 166° C./2×10⁻⁵ mmHg (yield: 62%).

On this fraction, measurements of an infrared absorption spectrum and NMR spectrum and elementary analysis were carried out to obtain the results shown below. From the results, this fraction was identified to be a compound represented by the following formula:

$$\underset{(a)}{H_2C}=\underset{\underset{O}{\|}}{\underset{(b)}{\overset{CH_3}{\underset{|}{C}}}}-\underset{(c)(d)(e)}{OCH_2CH_2CH_2}-\underset{\underset{CH_3}{\underset{|}{(f)}}}{\overset{(f)}{\overset{CH_3}{\underset{|}{Si}}}}-O-\underset{\underset{CH_3}{\underset{|}{(f)}}}{\overset{(f)}{\overset{CH_3}{\underset{|}{Si}}}}-\underset{(g)(h)(i)}{CH_2CH_2CH_2N}\underset{\underset{O}{\|}}{\overset{\overset{H}{\underset{|}{(j)}}}{C}}CF(OCF_2-CF)_{\overline{3}}OC_3H_7$$
$$\overset{|}{CF_3}$$

where (a) to (j) indicate the respective protons (indicating the same hereinafter in this example).

Infrared absorption spectrum: cm⁻¹: 3350 (acid amide >NH), 1720 (ester >C=O), 1715 (acid amide >C=O), 1640 (vinyl >C=CH₂).

NMR spectrum: ppm (δ): 7.67 (broad s, 1H, (j)), 5.94 (s, 1H, (a)), 5.34 (s, 1H, (a)), 4.08–3.85 (t, 2H, (c)), 3.44–3.0 (m, 2H, (i)), 1.80 (s, 3H, (b)), 1.71–1.28 (m, 4H, (d), (h)), 0.70–0.21 (m, 4H, (e), (g)), −0.02 (s, 12H, (f)).

| | Elementary analysis: % | | | |
|---|---|---|---|---|
| | C | H | Si | F |
| Calculated: | 30.89 | 2.68 | 4.98 | 48.86 |
| Found: | 31.02 | 2.78 | 4.98 | 48.74 |

EXAMPLE 4

To 50 g (0.09 mol) of N-allyl acid amide (III, n=1) obtained in the same manner as in Example 1, 0.1 g of BHT and 1 ml of a toluene solution containing 1% of chloroplatinic acid were added, and the mixture was heated to 90° C. and 41 g (0.1 mol) of a methacrylic acid ester having a silicon-bonded hydrogen atom, represented by Formula:

$$H_2C=\underset{\underset{O}{\|}}{\overset{\overset{CH_3}{\underset{|}{C}}}{C}}-OCH_2CH_2CH_2-(\underset{\underset{CH_3}{\underset{|}{}}}{\overset{CH_3}{\underset{|}{Si}}}-O)_{\overline{3}}\underset{\underset{CH_3}{\underset{|}{}}}{\overset{CH_3}{\underset{|}{Si}}}-H$$

was dropwise added thereto. After the addition, the mixture was stirred for further 1 hour, and thereafter cooled, followed by separation of the reaction mixture by silica gel column chromatography to obtain 41 g of a product (yield: 45%). On this product, measurements of an infrared absorption spectrum and NMR spectrum and elementary analysis were carried out to obtain the results shown below. From the results, this product was identified to be a compound represented by the following formula:

$$\underset{(a)}{H_2C}=\underset{\underset{O}{\|}}{\underset{(b)}{\overset{CH_3}{\underset{|}{C}}}}-\underset{(c)(d)(e)}{OCH_2CH_2CH_2}-(\underset{\underset{CH_3}{\underset{|}{(f)}}}{\overset{(f)}{\overset{CH_3}{\underset{|}{Si}}}}-O)_{\overline{3}}\underset{\underset{CH_3}{\underset{|}{(f)}}}{\overset{(f)}{\overset{CH_3}{\underset{|}{Si}}}}-\underset{(g)(h)(i)}{CH_2CH_2CH_2N}\underset{\underset{O}{\|}}{\overset{\overset{H}{\underset{|}{(j)}}}{C}}CF-O-CF_2CF-OC_3F_7$$
$$\overset{|}{CF_3} \quad \overset{|}{CF_3}$$

where (a) to (j) indicate the respective protons (indicating the same hereinafter in this example).

Infrared absorption spectrum: cm⁻¹: 3350 (acid amide >NH), 1720 (ester >C=O), 1710 (acid amide >C=O), 1640 (vinyl >C=CH₂). NMR spectrum: ppm(δ): 7.70 (broad s, 1H, (j)), 5.95 (s, 1H, (a)), 5.36 (s, 1H, (a)), 4.10–3.83 (t, 2H, (c)), 3.40–3.00 (m, 2H, (i)), 1.78 (s, 3H, (b)), 1.70–1.20 (m, 4H, (d), (h)), 0.70–0.06 (m, 4H, (e), (g)), −0.03 (m, 24H, (f)).

| | Elementary analysis: % | | | |
|---|---|---|---|---|
| | C | H | Si | F |
| Calculated: | 34.36 | 4.49 | 11.90 | 34.21 |
| Found: | 34.62 | 4.21 | 11.68 | 34.46 |

EXAMPLE 5

To 30 g (0.05 mol) of N-allyl acid amide (III, n=1) obtained in the same manner as in Example 1, 0.05 g of BHT and 0.5 ml of a toluene solution containing 1% of chloroplatinic acid were added, and the mixture was heated to 90° C. and 28 g (0.05 mol) of a methacrylic acid ester having a silicon-bonded hydrogen atom, represented by Formula:

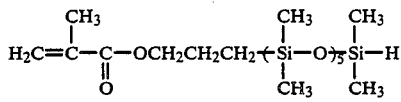

was dropwise added thereto. After the addition, the mixture was stirred for further 1 hour, and thereafter cooled, followed by separation of the reaction mixture by silica gel column chromatography to obtain 18 g of a product (yield: 30%). On this product, measurements of an infrared absorption spectrum and NMR spectrum and elementary analysis were carried out to obtain the results shown below. From the results, this product was identified to be a compound represented by the following formula:

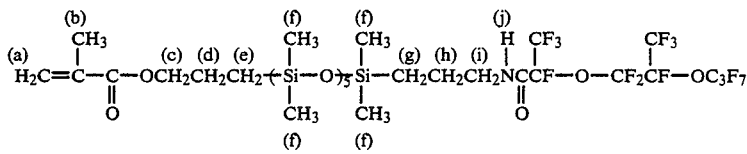

where (a) to (j) indicate respective protons (indicating the same hereinafter in this example).

Infrared absorption spectrum: $cm^{-1}$. 3350 (acid amide >NH), 1720 (ester >C=O), 1710 (acid amide >C=O), 1640 (vinyl >C=CH$_2$).

NMR spectrum: ppm (δ): 7.74 (broad s, 1H, (j)), 5.92 (s, 1H, (a)), 5.33 (s, 1H, (a)), 4.05–4.80 (t, 2H, (c)), 3.40–2.98 (m, 2H, (i)), 1.76 (s, 3H, (b)), 1.66–1.22 (m, 4H, (d), (h)), 0.62–0.05 (m, 4H, (e), (g)), −0.06−−0.30 (m, 36H, (f)).

| | Elementary analysis: % | | | |
|---|---|---|---|---|
| | C | H | Si | F |
| Calculated: | 34.09 | 4.98 | 15.43 | 29.57 |
| Found: | 34.27 | 4.82 | 15.18 | 29.31 |

What we claim is:

1. A methacrylic acid ester represented by General Formula (I):

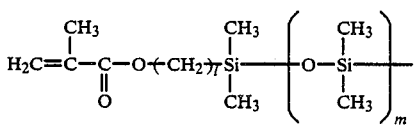

-continued

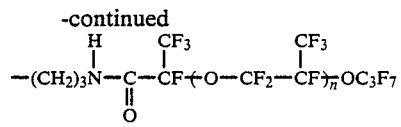

wherein l is an integer of 1 to 3; m is an integer of 1 to 10; and n is an integer of 1 to 3.

2. The methacrylic acid ester according to claim 1, which is represented by said General Formula wherein l is 3, m is 1 to 5 and n is 1 to 3.

3. A process for producing the methacrylic acid ester represented by the above General Formula (I):

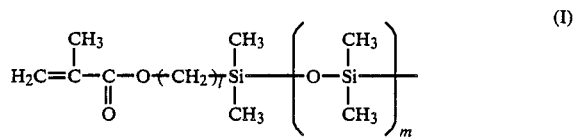

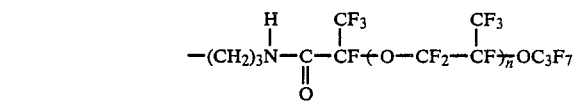

wherein l is an integer of 1 to 3; m is an integer of 1 to 10; and n is an integer of 1 to 3, comprising reacting an acid fluoride of poly(hexafluoropropylene glycol) represented by Formula (II):

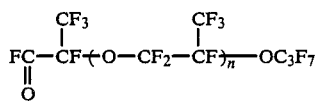

wherein n is as defined above,
with allylamine to produce an N-allyl acid amide represented by Formula (III):

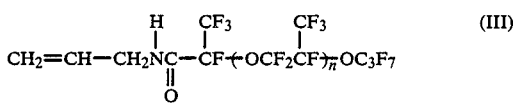

and reacting said N-allyl acid amide with a methacrylic acid ester represented by Formula (IV):

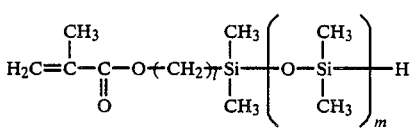

in the presence of a platinum catalyst.

* * * * *